US009039599B2

(12) United States Patent
Imboden et al.

(10) Patent No.: US 9,039,599 B2
(45) Date of Patent: May 26, 2015

(54) VIBRATORY ASSEMBLY FOR ARTICULATING MEMBERS

(71) Applicant: JJ ACQUISITION, LLC, San Francisco, CA (US)

(72) Inventors: Ethan Frederic Imboden, San Francisco, CA (US); Jeff Wyatt, Bozeman, MT (US)

(73) Assignee: JJ Acquisition, LLC, San Francisco, CA (US)

( * ) Notice: Subject to any disclaimer, the term of this patent is extended or adjusted under 35 U.S.C. 154(b) by 51 days.

(21) Appl. No.: 13/662,198

(22) Filed: Oct. 26, 2012

(65) Prior Publication Data

US 2013/0109914 A1 May 2, 2013

Related U.S. Application Data

(60) Provisional application No. 61/551,837, filed on Oct. 26, 2011, provisional application No. 61/551,845, filed on Oct. 26, 2011, provisional application No. 61/709,121, filed on Oct. 2, 2012.

(51) Int. Cl.

| | |
|---|---|
| ***A61F 5/00*** | (2006.01) |
| ***A61H 19/00*** | (2006.01) |
| ***A61H 1/00*** | (2006.01) |
| ***A61H 23/02*** | (2006.01) |

(52) U.S. Cl.

CPC .................. *A61H 19/00* (2013.01); *A61H 1/00* (2013.01); *A61H 2201/0111* (2013.01); *A61H 19/30* (2013.01); *A61H 19/34* (2013.01); *A61H 23/0218* (2013.01); *A61H 23/0245* (2013.01); *A61H 23/0263* (2013.01); *A61H 2201/0188* (2013.01); *A61H 2201/164* (2013.01); *A61H 2201/165* (2013.01); *A61H 2201/501* (2013.01); *A61H 2201/5097* (2013.01); *A61H 2201/1683* (2013.01)

(58) Field of Classification Search

USPC .......... 600/38–41; 601/11, 46, 67, 69, 70, 72, 601/74, 78, 79, 80

See application file for complete search history.

(56) References Cited

U.S. PATENT DOCUMENTS

| | | | | |
|---|---|---|---|---|
| 3,996,930 | A | 12/1976 | Sekulich | 128/67 |
| 5,853,362 | A | 12/1998 | Jacobs | 600/38 |
| 6,132,366 | A | 10/2000 | Ritchie et al. | 600/38 |
| 6,203,509 | B1 | 3/2001 | Duboff | |
| RE38,924 | E | 12/2005 | Ritchie et al. | 600/38 |

(Continued)

FOREIGN PATENT DOCUMENTS

| | | |
|---|---|---|
| CA | 2 471 525 | 3/2005 |
| EP | 1 477 149 A1 | 11/2004 |

(Continued)

OTHER PUBLICATIONS

International Search Report for PCT/US2012/062160 mailed Mar. 19, 2013.

*Primary Examiner* — John Lacyk

(74) *Attorney, Agent, or Firm* — Manuel de la Cerra

(57) ABSTRACT

A vibratory assembly is provided that incorporates a vibratory mechanism worn by a sexual participant on one or more digits of an articulating member for the sexual exploration and stimulation of erogenous zones. A modular erogenous stimulation system including the vibratory assembly is also provided along with a kit for providing erogenous stimulation to at least one participant.

20 Claims, 7 Drawing Sheets

(56) References Cited

U.S. PATENT DOCUMENTS

| | | | | |
|---|---|---|---|---|
| 7,081,087 | B2 | 7/2006 | Jannuzzi | 600/38 |
| 7,452,326 | B2 | 11/2008 | Fladl et al. | 600/38 |
| 7,510,537 | B2 | 3/2009 | Imboden et al. | 601/70 |
| 7,530,944 | B1 | 5/2009 | Kain | 600/38 |
| D605,779 | S | 12/2009 | Murison | D24/215 |
| 7,828,717 | B2 | 11/2010 | Lee | 600/38 |
| 2003/0083598 | A1 | 5/2003 | Kobayashi et al. | |
| 2003/0195441 | A1 | 10/2003 | Firouzgar | 301/46 |
| 2003/0221238 | A1 | 12/2003 | Duboff et al. | |
| 2004/0230093 | A1 | 11/2004 | Marshall | 600/38 |
| 2005/0203335 | A1 | 9/2005 | Stachon | 600/39 |
| 2006/0141903 | A1 | 6/2006 | Gardos et al. | 446/490 |
| 2008/0009775 | A1 | 1/2008 | Murison | 601/46 |
| 2008/0027275 | A1 | 1/2008 | Topolev | 600/38 |
| 2008/0077058 | A1 | 3/2008 | Klearman | |
| 2008/0113854 | A1 | 5/2008 | Ferri | |

FOREIGN PATENT DOCUMENTS

| | | | |
|---|---|---|---|
| EP | 1974710 | A1 | 10/2008 |
| GB | 0893868 | A | 4/1962 |
| GB | 2 401 551 | B | 11/2004 |
| WO | 2013063420 | A1 | 5/2013 |

VIBRATORY ASSEMBLY FOR ARTICULATING MEMBERS

FIELD OF THE INVENTION

This invention relates to vibratory devices, and in particular to compact vibratory massager applications.

BACKGROUND

Numerous sexual stimulation devices have been developed for use by individuals to derive sexual satisfaction individually or with one or more partners. These devices, which may be strictly manual or may include a stimulating feature such as a vibrating mechanism, can be used with respect to female anatomy, either internally to stimulate the vagina, or externally to stimulate the clitoris. Depending on their design features, some devices may also be used with respect to male anatomy to provide penal, scrotal and/or anal stimulation, either on their own or in combination with features that stimulate female anatomy. Both sexes may implement such devices and complements thereof for anal stimulation and stimulation of other erogenous anatomical regions.

Despite these known devices, a need persists for improved approaches for sexual exploration and enjoyment. For example, many existing systems are bulky, have poor functionality or are intimidating to most consumers. These and additional attributes are provided by devices disclosed herein that are intuitively used by individuals, couples and groups for optimizing sexual stimulation and discovering limitless options for deriving individual and mutual satisfaction therefrom.

SUMMARY

Devices, systems and kits are provided for achieving enhanced sexual stimulation via vibratory mechanisms worn on a participant's articulating members. A vibratory assembly for articulating members of a participant is provided that includes a vibratory mechanism having at least one motive source in electrical communication with a power source. The vibratory mechanism includes at least one vibration pod in which the motive source is housed and at least one pad having a lumen for insertion of the vibration pod therewithin. The power source is located externally of the motive source.

The vibratory assembly may further include a power source in a housing and connected in parallel via a cable with the vibratory mechanism. The power source is selected from a standard battery, a rechargeable battery and a specialized battery operational with the vibratory mechanism. One of the power source and the housing selectively includes at least one of a power switch and a participant interface thereon. The housing for the power source may includes at least one attachment member in detachable connection therewith. A wristband may be provided having a sheath within which the power source is retained during use of the vibratory assembly.

The vibration pod includes a pod housing in which the motive source is disposed in electrical communication with the power source. The pod housing contains at least two wires forming a circuit between the motive source and an external device to control and power the motive source using a cable that contains the wires.

The pod housing has a predetermined length, a predetermined width and a predetermined height that provides the pod housing with a generally low profile and a size adapted to be worn on at least one of the articulating members. The pod housing may include at least a first housing element and a second housing element enveloping the motive source thereby. The vibration pod, or the housing thereof, includes a thickness to width ratio in orange from about ¼ to about ½. The thickness may include a distance between a finger and a surface touched by the finger, and the width may include a finger width. In some embodiments, the vibrator pod is adapted for use with fingers having a width in a range from about 10 mm to about 20 mm. In a preferred embodiment, the pod housing has a thickness in a range from about 1.50 mm to about 2 mm with an inner wall thickness of about 0.78 mm and an outer wall thickness of about 1.5 mm. The vibration pod can be configured with respect to respective distances from a fingertip to a first knuckle on a finger and from the first knuckle to a second knuckle on the finger.

The motive source includes one or motors with the motors being selected from a motor fitted with an eccentric rotating weight, a solenoid actuator, a piezoelectric actuator, a cylindrical motor, a pan motor and combinations and equivalents thereof. In a preferred embodiment, the motive source is a coin-shaped pan motor having a diameter at or about 12 mm and a thickness at or about 3.4 mm.

The vibration pad includes a body having one or more attachment loops integral therewith. The pad body includes an external surface with elongate opposed side surfaces, opposed longitudinal surfaces, opposed extents and an internal surface delineating a lumen thereby. The lumen terminates at an opening provided at one or more of the opposed extents.

Each loop includes an arc connecting hinged extents of the loop disposed along the pad body and defining an orifice through which a participant inserts at least one digit of an articulating member. The hinged extents depend generally from opposed side surfaces of the pad body such that each loop is offset from a longitudinal axis of the pad body. The arc is pivotable along the pad body so that the arc may be rotated between an upright position relative to a longitudinal surface of the pad body and an inverted position relative to an opposed longitudinal surface of the pad body so that one or more digits of different sizes are insertable through the orifice. In some embodiments, at least one of the pad body and the loops incorporates at least one of a tactile element selected from a group of tactile elements including protrusions and recesses, and an aesthetic element selected from a group of aesthetic elements including one or more colors, materials, patterns and embellishments. The pad is fabricated from a material selected from silicone, thermoplastic elastomer (TPE), thermoplastic rubber (TPR) and combinations and equivalents thereof.

The vibration pod and vibration pad may be provided as an assembly with one or more pods insertable into one or more corresponding pads.

The vibratory assembly may be in communication with at least one remote control communicating signals thereto. One or more controllers can be in wireless communication with the vibratory assembly over a network.

A modular erogenous stimulation system is provided that includes a vibratory assembly as described herein. The system can include a plurality of interchangeable vibrator components and a power source. At least one of the plurality of interchangeable vibrator components and the vibratory assembly may be in communication with at least one remote control communicating signals thereto. At least one of the plurality of interchangeable vibrator components and the vibratory assembly may be a network-connected device in communication with one or more computing devices running at least one software application thereon.

A kit for providing erogenous stimulation to at least one participant is provided that includes one or more vibratory assemblies for articulating members of at least one participant. Each vibratory assembly includes a vibratory mechanism having at least one motive source in electrical communication with a power source. The vibratory mechanism incorporates one or more vibration pods each housing at least one motive source thereby, and one or more pads each having a lumen for insertion of one or more vibration pods therewithin. The power source is located externally of the motive source. In this kit, the vibration pods and the pads may be selectively interchangeable. The kit may further include a network-connected device in communication with one or more computing devices running at least one software application thereon.

A vibratory massager for applying stimulation to human erogenous zones is provided that includes a vibration pod. The vibration pod has a housing with a plurality of exterior surfaces and a non-linear periphery. The vibration pod also has at least one motive source retained by the housing. The housing has a generally low profile implemented at least by having a thickness to width ratio in a range from about ¼ to about ½ and a size adapted to be worn on an articulating member for massaging application to a surface of a human body. The housing contains at least two wires forming a circuit between the motive source and an external device, spaced apart from the vibration pod, that controls and powers the motive source using a cable that contains the wires. The vibratory massager may additionally incorporate the external device. In an exemplary embodiment, the external device and the pod are spaced apart by at least 6 inches.

The vibratory massager may include another vibration pod, with the two pods connected to each other via a free-standing cable.

A vibratory assembly is provided that includes a vibration pod as described herein and at least one silicone pad having at a body with one or more attachment loops integral therewith.

A vibratory massager for applying stimulation to human erogenous zones is provided that includes a vibration pod. The vibration pod includes a housing having a plurality of exterior surfaces forming an interior cavity for housing a motive source. The housing has at least one generally flat exterior surface and a non-linear periphery. The vibration pod additionally includes at least one motive source retained by the housing within the cavity and positioned to abut the flat exterior surface. The housing has a generally low profile implemented at least by having a thickness to width ratio in a range from about ¼ to about ½ and a size that a width of about 10 mm to 20 mm. The housing contains two wires forming a circuit between the at least one motive source and an external device, spaced apart from the vibration pod, that controls and powers the motive source using a cable that contains the wires.

BRIEF DESCRIPTION OF THE DRAWINGS

The nature and various advantages of the present invention will become more apparent upon consideration of the following detailed description, taken in conjunction with the accompanying drawings, in which like reference characters refer to like parts throughout, and in which.

DETAILED DESCRIPTION

Figure 1:
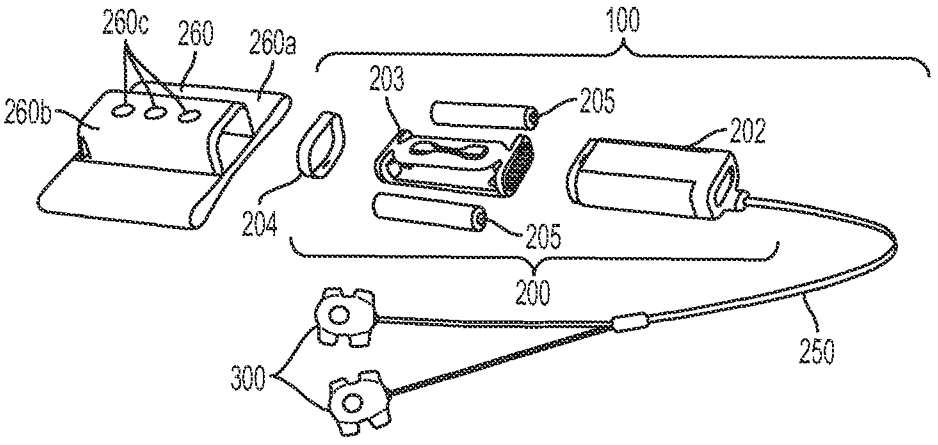
FIG. 1 shows an exploded view of an exemplary vibratory assembly for articulating members.

Now referring to the figures, wherein like numbers represent like elements, and with particular reference to FIG. 1, a vibratory assembly 100 is provided that may be worn on articulating members, such as one or more digits of a participant's hands and feet. Although vibratory assembly 100 is described herein with respect to articulating members, it is contemplated that vibratory assembly 100 is also amenable for use vaginally, anally and in contact with portions of the penis and/or scrotum. Vibratory assembly 100 may incorporate all of the features of co-owned U.S. Application No. 61/709,121, the entire disclosure of which is incorporated by reference herein. Vibratory assembly 100 is also contemplated for use with prosthetic and orthotic devices and implements, and in combination with other sexual stimulation devices, including but not limited to those disclosed by Applicants' U.S. Application Nos. 61/551,837 and 61/551,845, the entire disclosures of which are incorporated by reference herein. As shown herein, vibratory assembly and the features thereof are not for subcutaneous insertion, nor are they for surgical insertion and attachment to internal organs.

Vibratory assembly 100 includes a dock 200 connected in parallel via a cable 250 with a vibratory mechanism (further described hereinbelow) that is worn by a participant on one or more digits of an articulating member (or with respect to one or more other anatomical areas as described herein). Cable 250 can be a free standing, unsupported cable and may incorporate an electro-mechanical connector at an end thereof that is connected using, for example, a friction-fit connection, to a power/controller device.

A power source such as power pack 203 and any associated control electronics may be housed within dock housing 202 along with a printed circuit board (not shown) that mechanically supports and electrically connects dock 200 with the vibratory mechanism. Dock housing 200 retains power pack 203 therein with the power pack being protected by a closure such as removable end cap 204.

Power pack 203 incorporates one or more power sources, such as a battery source depicted herein as a pair of AAAA batteries 205. When a battery source is used, the battery source may be selected from any standard battery, any rechargeable battery and any specialized type battery that satisfies the operational duration and power needs of vibratory assembly 100. If a rechargeable battery pack is employed as the power source, such battery pack may be inductively rechargeable or reversibly, physically connected to a recharging device. Such a rechargeable pack may be selected from known rechargeable configurations, including but not limited to lithium ion, nickel-metal-hydride, nickel cadmium and lithium polymer.

Figure 2:
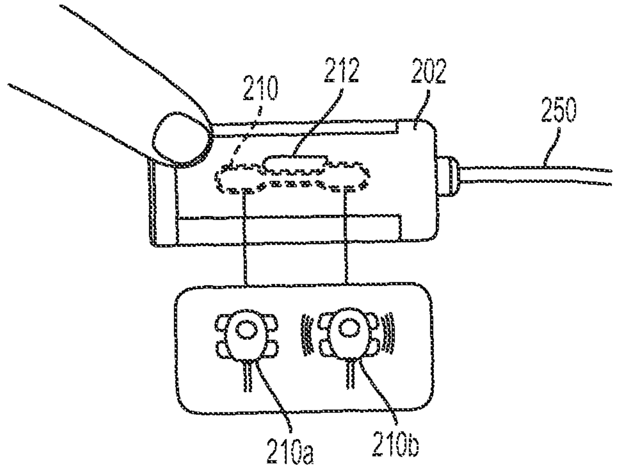
FIG. 2 shows a top perspective view of a dock having an exemplary on/off switch and user interface thereon.

Referring further to FIG. 2, dock housing 202 may include an "on/off" switch 210 thereon that controls delivery of power to the vibratory mechanism via a push-button switch under spring tension). Dock housing 202 may also include a participant interface, either via on/off switch 210 or via a separate interface (not shown) for controlling electrical connection of the power source to an associated vibratory mechanism. For example, as shown in FIG. 2, on/off switch 210 may include an exemplary intensity control interface 212 to provide a plurality of selectable intensity level settings and/or pulsed or waveform signals that vary the vibratory intensity over time. On/off switch 210 and any associated control interface may include indicia incorporated on dock housing 202 or power pack 203 to provide participants with an intuitive visual indication of vibration control. Such indicia, which may be visual, tactile and/or aural (and may include equivalents and combinations thereof), obviate distractions experienced by participants while adjusting a desired vibration effect. For example, exemplary indicia 210*a* and 210*b* depicted in FIG. 2 visually indicate the respective "off" and "on" states of vibratory assembly 100.

A participant interface may communicate commands and control signals to a control module associated with vibratory assembly 100 over a wireless connection. Applicants have addressed this need by providing erogenous stimulation systems and devices having upgradeability and interoperability that would allow a purchaser to enter the market for such stimulators at a reasonable price (see, for example, Applicants' U.S. Application Ser. Nos. 61/551,837 and 61/551,845, the entire disclosures of which are incorporated by reference herein). Applicants' disclosed systems and devices promote interchangeability and modularity for creation of multiple sexual experiences, and portability for encouragement of use in a variety of environments, thereby leading participants to realize favorable results. Participants can upgrade the functionality and expand their collection of devices over time without sacrificing the initial investment, due to the ability to interchange the modular components and capitalize on their cross-functionality.

Figure 3:
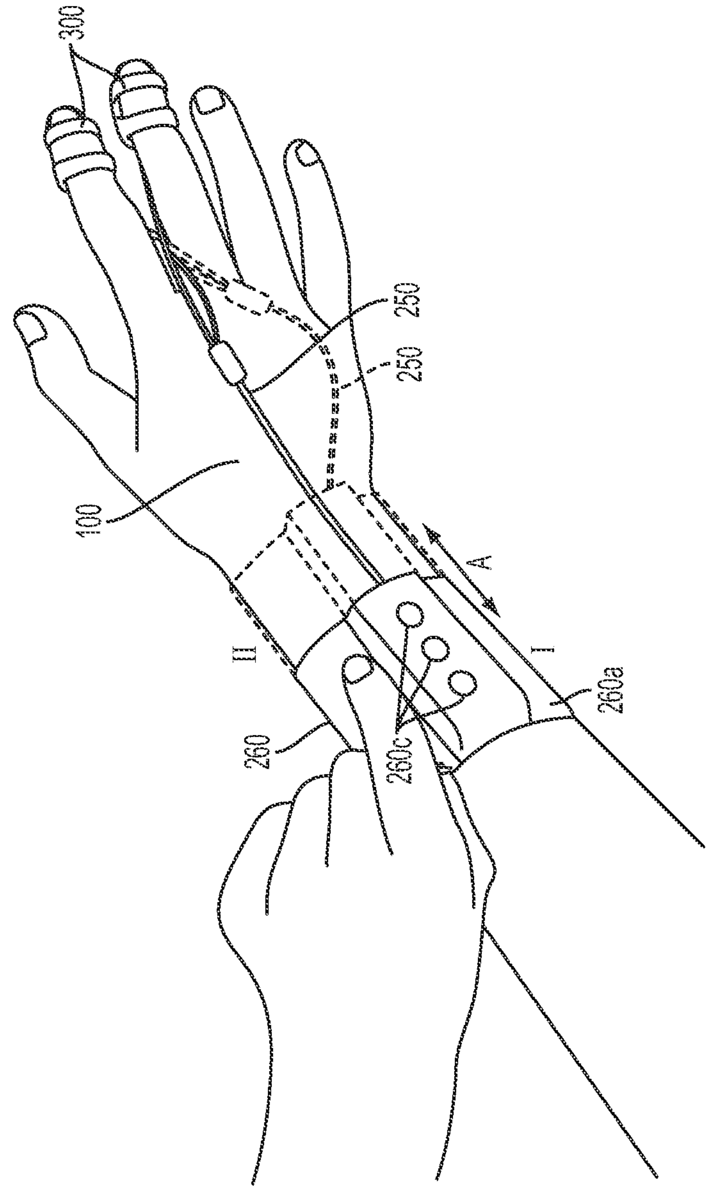
FIG. 3 shows a perspective view of the vibratory assembly of FIG. 1 in use as a fingertip massager.

As further shown in FIG. 3, vibratory assembly may be worn by a participant as a fingertip massager with dock 200 (not shown in FIG. 3) held in place along a participant's wrist and forearm by a wristband 260 (also shown in FIG. 1). Wristband 260 includes an attachment band 260*a* and a dock sheath 260*b* for retention of dock 200 thereby. Wristband 260 may also include control indicia 260*c* thereon that correspond to at least one of on/off switch 210 and control interface 212. In this example, participants may adjust vibratory control settings as desired without touching dock 200 or adjusting vibratory assembly 100.

Wristband 260 is desirably fabricated from a material having elastic properties (fix example neoprene, elastic textiles and the like). Such material selection permits wristband 260 to be work on wrists and arms of different sizes and also permits adjustment of the wristband along a single participant's arm. For example, in position I shown in FIG. 3, wristband 260 is provided along a participant's forearm with cable 250 remaining taut during use of vibratory assembly 100. Wristband 260 may be maneuvered along arrow A between position I and position II (and anywhere therebetween), in which position cable 250 is provided some slack. In position II, the participants' fingers may, for example, explore deeper penetration or greater degrees of rotational freedom in attainment of sexual satisfaction. Although FIG. 3 shows vibratory assembly 100 worn on a participant's wrist, a complementary band may permit dock 200 to be worn by a participant on an ankle, a belt loop, an undergarment and other locations proximate to one or more articulating members white ensuring non-obstructive retention of the dock during use of vibratory assembly 100.

As an alternative, or in addition, to wristband 260 and its equivalents, dock housing 202 may further include structure to facilitate detachable connection of one or more attachment members (not shown). Such structure may include one or more recesses, notches, slots or complementary or equivalent means to facilitate detachable connection of attachment members, including one or more plastic or leather straps, one or more elastic bands, one or more textile swatches, one or magnetic clasps and the like. One or more attachment members may also be integral with dock housing 202 with additional attachment members selectively provided to accommodate a variety of participant anatomies (e.g., longer length attachment members for wider wrists and ankles) or participant preferences (e.g., a plurality of attachment members having a variety of aesthetic features, including but not limited to colors, materials, embellishments, themes and/or other decorative features).

As shown in FIGS. 1 and 3, an exemplary vibratory mechanism is provided as one or more digit assemblies 300. Each digit assembly 300 includes at least one vibration pod 302 (or "pod" as further shown and described with respect to FIGS. 4, 5 and 5A) enveloped by a vibration pad 304 (or "pad" as further shown and described with respect to FIGS. 4 and 5). In a preferred embodiment, digit assembly has a predetermined volume in a range of about 2 cc to about 4 cc, and a more preferred volume of about 3 cc.

Vibration pod 302 can be used with a plurality of different flexible forms of pad 304 that provide different functional application as a results of the profile and shape thereof. Vibratory assembly can therefore change, for example, from being a fingertip massager (as shown in FIG. 3) to a toe massager, an integrated garment massager (for example, by placing pod 302 and an associated flexible form with an undergarment), a massager placed in combination with one or more sexual stimulation devices and equivalents and combinations thereof. The attached additional disclosure provides additional pad configurations that may be used with pod 302.

Vibration pod 302 includes a pod housing 306 having a predetermined length L, a predetermined width W and a predetermined height H that provides pod housing 306 with a generally low profile and a size adapted to be worn on at least one of the articulating members. In an exemplary embodiment, housing 306 exhibits a thickness (e.g., a distance between a finger and the surface touched thereby) to width (e.g., corresponding to a finger width) ratio in a range from about ¼ to ½. In a preferred embodiment, pod housing 306 has a thickness in orange from about 1.50 mm to about 2 mm with an inner wall thickness of about 0.78 mm and an outer wall thickness of about 1.5 mm. Other exemplary parameters contemplated for the profile of pod housing 306 include known ranges of widths and diameters of adult fingers. Although a broad range of widths and diameters are contemplated, a mean range would encompasses finger widths and diameters in a range from about 10 mm to about 20 mm. Also, housing 306 may be configured with respect to respective distances from a fingertip to the first knuckle from the first knuckle to the second knuckle (for example when digit assembly 300 is worn in different positions along a finger length, or multiple digit assemblies 300 are worn on the same or different fingers anywhere along the length thereof). It is understood that ranges of widths and diameters of adult toes and other articulating members are also contemplated by the low profile of housing 306. Consideration of these parameters ensures that housing 306 remains unobtrusive, that is, it does not extend too far in any direction from the shape of a finger (or other articulating member) adorning one or more digit assemblies 300.

Figure 4:
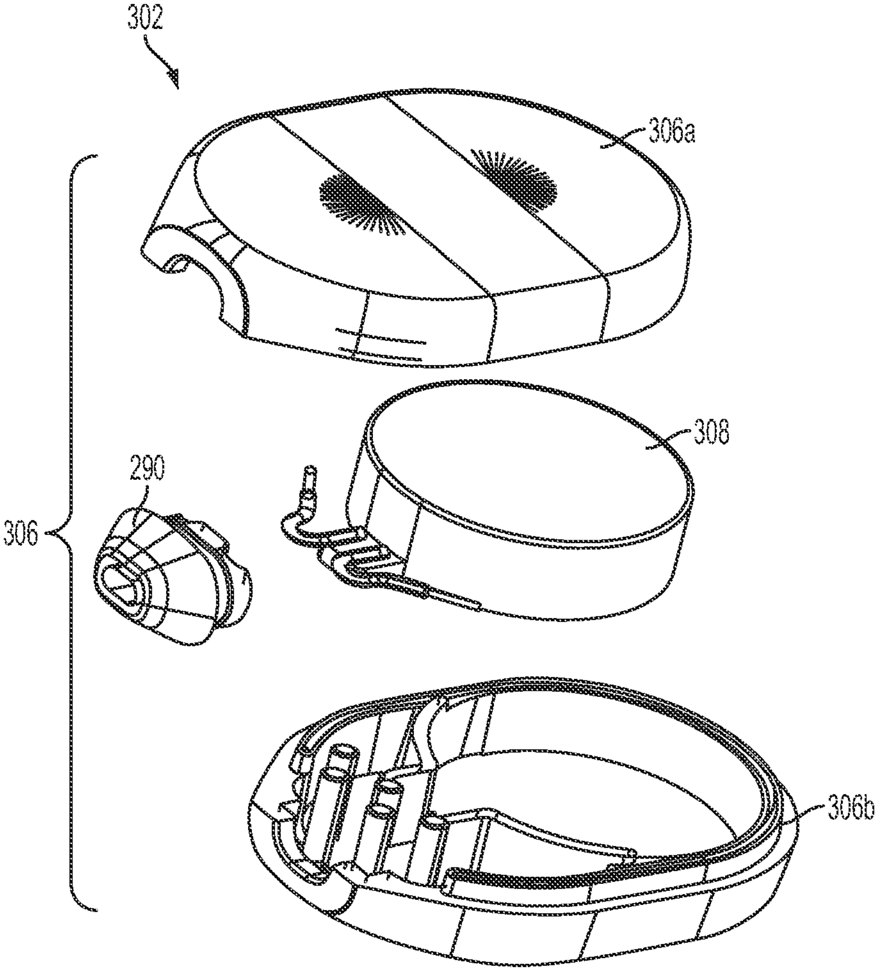
FIG. 4 shows an exploded view of an exemplary vibration pod used with the vibratory assembly of FIG. 1.
Figure 5A:
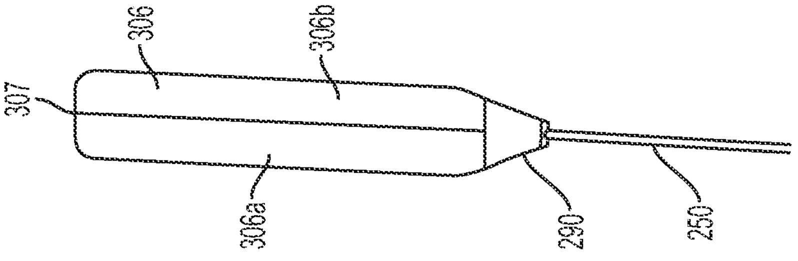
FIG. 5A shows a side view of the vibration pod of FIG. 4.
Figure 5:
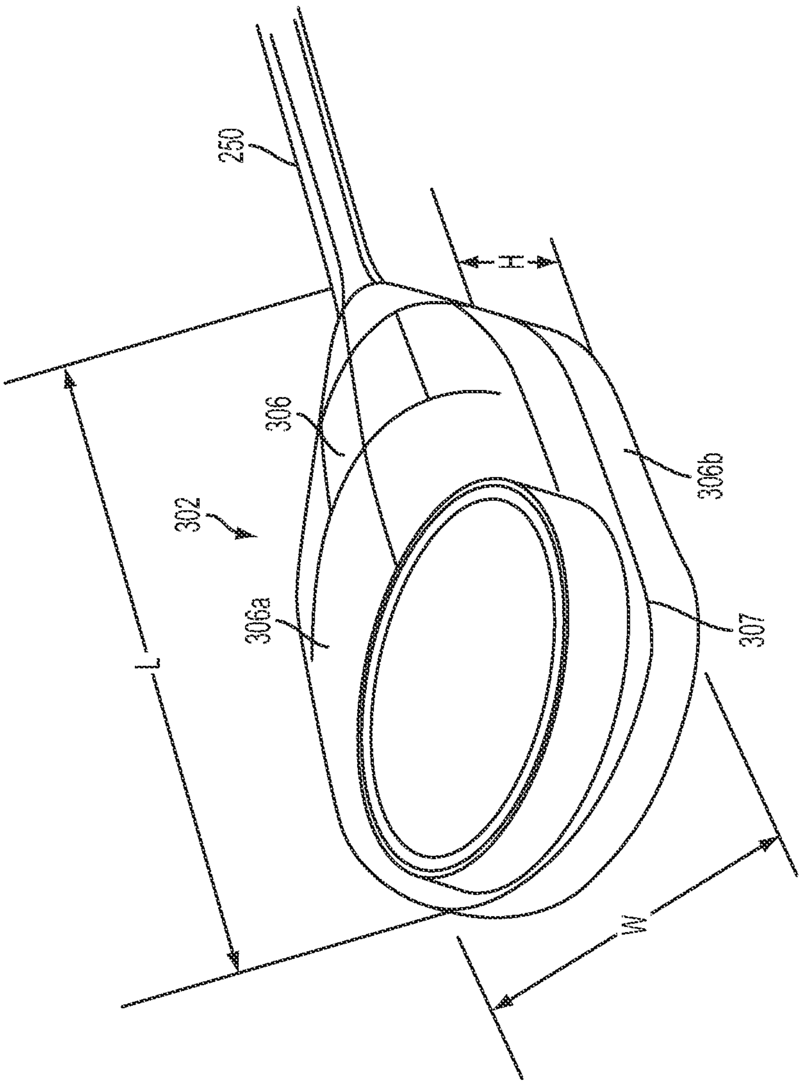
FIG. 5 shows a top perspective view of the vibration pod of FIG. 4.

In a preferred embodiment, pod housing 306 includes two pieces that are attached together to form the assembled housing. In FIGS. 4, 5 and 5A, pod housing 306 is shown with at least a first housing element 306*a* and a second housing element 306*b* which together envelop at least one motive source 308 thereby. First and second housing elements 306*a*, 306*b* may be affixed to one another, for example, along an ultrasonic weld line 307 having epoxy applied thereat to ensure waterproofing. If desired, first and second pod housing elements 306*a*, 306*b* may be connected by other known attachment means, including but not limited to snap-tight engagement, notch and recess engagement, threaded engagement and any equivalent and combination thereof. Pod housing 306 may comprise more or fewer housing elements without departing from the scope of Applicants' disclosure. If desired, pod 302 may be configured to have a female or male connection that can be used to connect pod 302 to other vibratory components. Such vibratory components may include, but are not limited to, one or more other massagers, one or more cables and one or more motive sources. Such a feature enables the creation of a chain of pods in operative communication with one another for enjoyment by one or plural participants.

Pod housing 306 is shown as a generally elliptical member (e.g., as shown, generally elliptical in lateral cross-section and generally rectangular in vertical cross section) with first and second housing elements 306*a*, 306*b* shown as generally symmetrical members in corresponding engagement with one another. It is understood that pod housing 306, as well as first and second housing elements 306*a*, 306*b* thereof, are not limited to the illustrated geometry and may have other geometry amenable to practice of the presently disclosed vibratory device. For example, pod housing 306 may exhibit a generally rectangular structure having rounded edges and corners, although other cuboid, cylindrical, spherical, ovoid and other shapes and configurations could be employed. These geometries, along with other complementary geometries (including geometries in which at least a portion of the housing exhibits a non-linear periphery, that is, geometries in which at least a portion of the housing exhibits rounded edges), may, if desired, avoid sharp corners and edges that may poke, pinch or scratch a wearer or partner during handling, use and maintenance of the vibratory assembly. The shape and size is preferably configured to be easily inserted in or removed from a pad in a flexible body by simple manipulation.

Either or both of first and second housing elements 306*a*, 306*b* may be fabricated from a readily available and formable thermoplastic such as polycarbonate (PC). Other materials may be selected for fabrication of the first and second housing elements, which include but are not limited to, acrylonitrile butadiene styrene (ABS) and a PC/ABS blend.

Pod housing 306 contains two or more wires (not shown) forming a circuit between a motive source 308 and dock 200 to control and power the motive source using cable 250 that contains the wires. At least one motive source 308 is connected in parallel with dock 200 via cable 250. Cable 250 may include strain relief 290 incorporated therewith (see FIGS. 4 and 5A) that permits cable 250 to move without detachment from motive source 308 (as is known in the art).

Motive source 308 may be selected from one or more motive or vibration sources, including but not limited to a motor fitted with an eccentric rotating weight, a solenoid actuator, a piezoelectric actuator, one or more cylindrical motors and other small vibration generating mechanisms as known. Exemplary vibratory devices may include a pan motor and a self-contained motor (with the tatter having an associated weight within a bullet-shaped enclosure, wherein the motor may be electrically connected to a power source and/or controller, as known. In an exemplary embodiment, motive source 308 is a coin-shaped pan motor having a diameter at or about 12 mm diameter and a thickness in a range from about 0.75 mm to about 5 mm. In a preferred embodiment, a pan motor employed in pod 302 has a thickness of about 14 mm. Such pan motors are commercially available in a variety of dimensional extents that are amenable to employment within low profile pod housing 306. Such pan motors can be particularly suited to providing enhanced vibrational performance while utilizing available surface area provide by the available physical dimensions. When more than one digit assembly 300 is contemplated, each associated vibration pod 302 may incorporate a unique motive source to achieve interchangeable vibratory effects. It is contemplated that individual pods may accommodate one or more motive source thereby to deliver an enhanced vibratory effect to the participant.

At least one vibration pod 302 may include an LED or other light source (not shown) that assists the participant with location of the pod. Such LED or light source may also be electively illuminated to generate a variety of light and color effects for enhancement of a sexual stimulation session.

Figure 6:
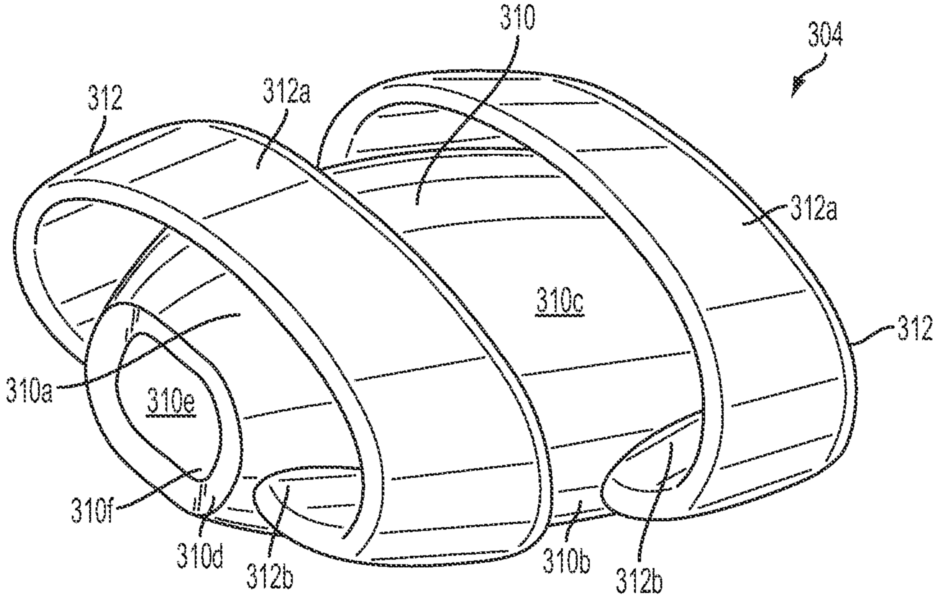
FIG. 6 shows a top perspective view of an exemplary vibration pad used with the vibratory assembly of FIG. 1.
Figure 6A:
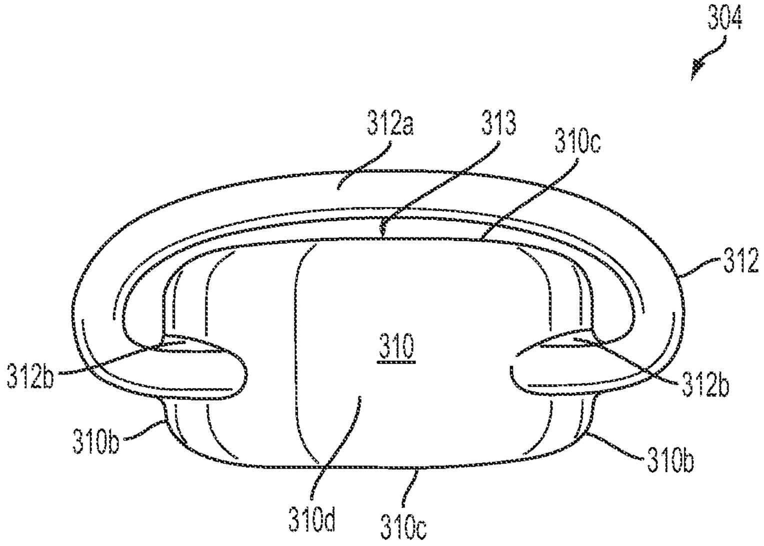
FIG. 6A shows a rear view of an exemplary vibration pad used with the vibratory assembly of FIG. 1.
Figure 6B:
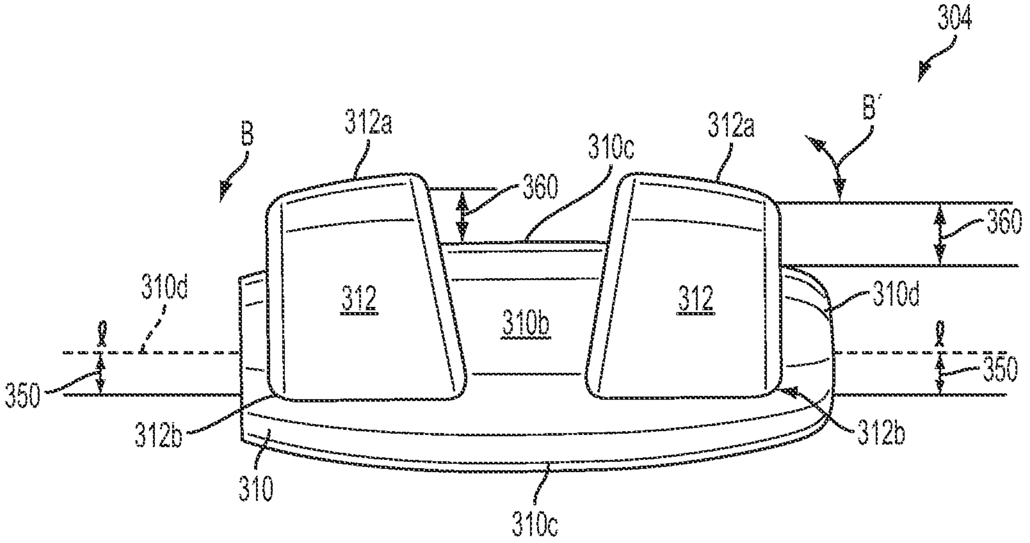
FIG. 6B shows a side view of the vibration pad of FIGS. 5 and 5A having loops in an upright position.
Figure 6C:
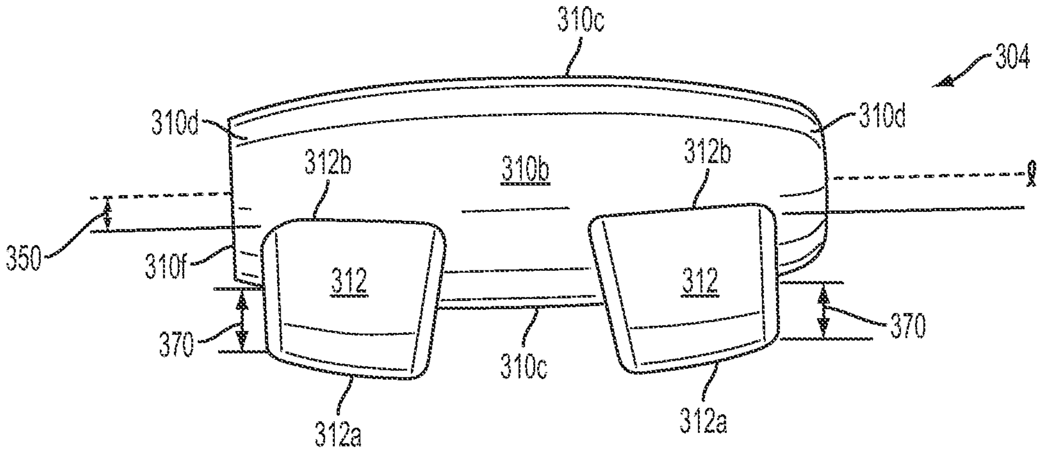
FIG. 6C shows the vibration pad of FIG. 6B having loops in an inverted position relative to a longitudinal surface of the pad body.
Figure 6D:
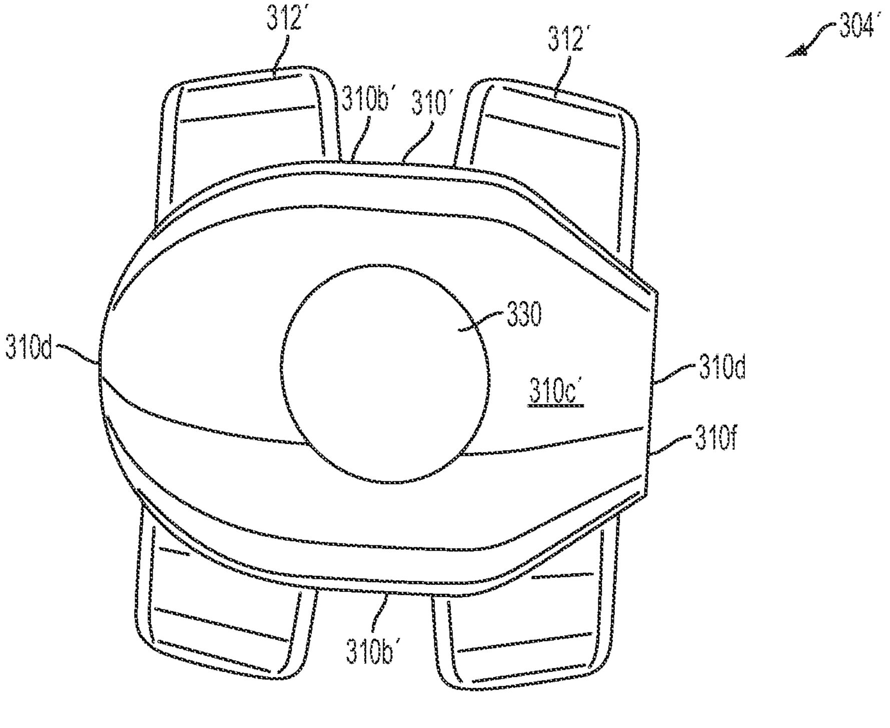
FIG. 6D shows an alternative embodiment of an exemplary vibration pad used with the vibratory assembly of FIG. 1.

Referring further to FIGS. 6 to 6D, pad 304 may be art integrally molded member having a body 310 with one or more digit attachment loops 312 affixed thereto. As shown, body 310 includes an external surface 310*a* having elongated opposed side surfaces 310*b*, opposed longitudinal surfaces 310*c*, opposed extents 310*d* and an internal surface delineating a lumen 310*e* thereby. Lumen 310*e* terminates with at least one extent 310*d* having an opening 310*f* thereat, although an opening may be provided at each extent 310*d* to accommodate insertion of a corresponding pod 302 into lumen 310*e*. In some embodiments, pad 304 may be molded over pod housing 306, other partially or in its entirety to encapsulate pod housing 306 thereby. One or more openings may then be provided along external surface 310*a* of pad body to enable direct placement of pod housing 306 against a region to be stimulated.

Pad body 310, as well as lumen 310*e* therein, may assume a geometry adapted for use with vibratory assembly 100. Lumen 310*e* may assume a particular geometry that complements the geometry of pod housing 306 residing therewithin during use of vibratory assembly 100. For example, a portion of external surface 310*a* of pad body 310 may be substantially flat to accommodate placement of a finger or toe pad thereon, white an opposed portion of external surface 310*a* of the pad is rounded or undulated to complement the anatomical contours of a vaginal, anal or other anatomical region. This example illustrates that pad body 310 need not be fabricated as a generally symmetrical member, although lumen 310*e* therein may still accommodate a generally symmetrical pod 302 thereby. Lumen 310*e* may also be configured to accept more than one vibration pod 302 therewithin.

Each loop 312 includes an arc 312*a* passing over a width of pad body 310 and connecting hinged extents 312*b* of the loop thereto. Arc 312*a* defines an orifice 313 through which a participant inserts at least one digit of one or more articulating members (e.g., one or more fingers, toes, implements and/or prosthetic/orthotic devices). Hinged extents 312*b* depend generally from opposed side surfaces 310*b* of pad body 310 such that each loop 312 is offset from a longitudinal extent l of pad body 310 (as particularly seen in FIGS. 6B and 6C). Orifice 303 delineates a predetermined clearance between arc 312*a* and a longitudinal surface 310*c* to accommodate articulating members of various sizes without requiring adaptation of arc to any particular participant's anatomical dimensions. Referring to FIGS. 6B and 6C, each loop 312 is pivotably arranged along pad body 310 so that arc 312*a* may be rotated between an upright position relative to a longitudinal surface 310*c* of the pad body (FIG. 6B) and an inverted position relative to an opposed longitudinal surface 310*c* of the pad body (FIG. 6C) so that one or more participant digits of different sizes are insertable through orifice 313. As shown in FIG. 6B, hinged extents 312 are shown as being offset from longitudinal axis e by a predetermined offset 350 that delineates a clearance 360 provided by orifice 313 between arc 312 and longitudinal surface 312. Loops 312 as shown in FIG. 6B may be rotated in the direction of arrows B and B' from a position with arc 312*a* bridging a first longitudinal surface 310*c* so that one or more digits are insertable there adjacent through orifice 311. After rotation of loops 312 in the direction of arrows B and B', loops 312 can assume a subsequent position as shown in FIG. 6C, wherein arc 312*a* bridges a second longitudinal surface 310*c* to accommodate insertion of one or more digits of different sizes through the same orifice 311. In the latter position, orifice 313 delineates a clearance 370 between arc 312*a* and second longitudinal surface 310*c*, which clearance differs from clearance 360 provided in the initial position of loops 312.

Orifice 313 therefore is enlarged or reduced in accordance with offset 350 to accommodate insertion of articulate members having a wide variety of dimensions as well as pairs and multiple of such articulate members. This feature permits participants to accommodate insertion of one or more digits, or to accommodate insertion of digits of varying sizes and contours, through orifice 313. This feature additionally permits partners to experiment with different uses of vibratory assembly 100. In an exemplary use of this feature, one loop 312 may be positioned with arc 312*a* bridging a first longitudinal surface 310*c* to accommodate insertion of a first participant's articulating member. Simultaneously, a second loop 312 may be rotated so that arc 312*a* thereof bridges a second longitudinal surface 310*c* to accommodate insertion of a second participant's articulating member. In another exemplary use of this feature, one or more loops may be selectively moved between upright and inverted positions to accommodate placement of one or more digit assemblies 300 relative to one or more of a distal phalange, the medial phalange and the proximal phalange of a participant's finger. In this example, retention of the articulating member through orifice 313 is ensured regardless of where along the articulating member the pad is placed. In the example shown in FIG. 3, wristband 260 may be adjusted along the participant's wrist or forearm while digit assemblies 300 are disposed as desired along one or more fingers without requiring enlargement or reduction of loops 312. These examples are merely illustrative, and the pivotable nature of loops 312 facilitates numerous articulating members in a variety of positions as would be understood in the art.

Pad 304 is not limited to the incorporation of a pair of loops as shown, and may include more or fewer loops to accommodate varying numbers and sizes of articulating members. For example, a single loop may be provided to accommodate large digits or to accommodate more than one articulating member during a sexual stimulation experience. In another example, multiple loops may be incorporated along pad body 310 to ensure a desired fit upon an articulating member.

Pad 304 may additionally incorporate tactile and aesthetic features on at least one of body 310 and one or more loops 312. For example, protrusions and/or recesses may be provided along at least a portion of pad body 310 (and/or along at least a portion of one or more of loops 312) to generate additional stimulation. Also, pad body 304 and/or loops may be provided in a variety of colors and designs corresponding to a desired ambience to be attained by the participant.

Referring to FIG. 6B, another exemplary pad 304' is shown having features commensurate with those provided on pad 304 and therefore designated by like numbers. Pad 304' includes a pad body 310' having surfaces commensurate with those described with respect to pad body 310. Pad 304' includes a protrusion or bump 330 extended outwardly from a longitudinal surface 310*c*' of pad body 310'. In a preferred embodiment, bump 330 is provided along a portion of longitudinal surface 310*c*' corresponding to placement of motive source 308 in pod housing 306. Bump 330 may vary in size and geometry relative to motive source 308 to effect transference of vibratory movement from the motive source to the anatomical region being stimulated. For example, bump 330 is shown as having a generally hemispherical geometry. Bump 330 may exhibit such geometry in combination with undulations, recesses and/or multiple bumps that provide a variety of stimulation experiences. Loops 312' of pad 304' are pivotable in the same manner as described herein with respect to pad 304.

Pad 304 may be fabricated from a generally elastic material with a suitable surface texture that resiliently supports vibration pod 302 therewithin and also provides the participant with a comfortable and enjoyable tactile sensation during use. The material comprising pad 304 may be selected from any biocompatible material, including hut not limited to silicone rubber, thermoplastic elastomer (TPE), thermoplastic rubber (TPR) and any other plastics, composites and equivalent and complementary materials as known. The selected material may vary in stiffness (for example, hard versus soft silicone moldings can provide varying levels of desire and controllability over the duration and level of applied intensity). For some embodiments, encasement of pod housing 306 entirety in silicone facilitates interchangeability and simplifies fabrication of the loops without. Silicone, whether partially or entirely encapsulating pod housing 306, also imbues digital assembly 300 with softness and sound dampening while ensuring a generally waterproof apparatus. It is contemplated that pad 304 (and 304') may incorporate a combination of silicone and thermoplastic in areas that contact directly the human body for enhancement of vibration transmission.

The selected material is further amenable to residence in or near a body orifice (e.g., vaginal or anal). The selected material is further amenable to prolonged exposure to bodily secretions and externally applied enhancements (e.g., food and beverage products, edible and non-edible lubricants and jellies, etc.) without being harmed or contaminated, and without itself harming or contaminating the participant. The selected material is also tactilely pleasurable on both external and internal tissues. The selected material should satisfy all applicable regulatory and safety standards, such as those established by the Food and Drug Administration (FDA) in the United States and commensurate standards established by governing bodies in other countries. The selected material should additionally be amenable to application of temperature differentials without deleterious effect to the performance of the vibratory assembly.

Vibratory assembly 100 is not limited to a pair of digit assemblies 300 as shown but may include more or fewer vibration pods 302 powered by dock 200. One or more digit assemblies 300 may be placed on a single articulating member for maximizing internal stimulation, for example, to achieve more or less penetration as desired. Digit assemblies 300 may be placed, for example, relative to one or more of the distal phalange, the medial phalange and the proximal phalange of a finger. Alternatively, a digit assembly 300 may be placed relative to one of these phalanges on one finger while another digit assembly 300 is placed relative to a different one of these phalanges on another finger. Comparable placements of vibration pods 302 are contemplated on one or more toes. These examples are not exhaustive, and any number of combinations of pad configurations and vibration pods are contemplated to augment interoperability of the vibratory assembly.

Vibratory assembly 100 may be responsive to a remote control having a sensor for receiving and processing external signals (as is known in the art). The remote control and sensor may be in wireless communication with one other, and potentially with a control module (for example, by using Zigbee™ or Bluetooth™ wireless communication protocols). One or more controllers may be interconnected over a wireless communication network to control operation of at least one vibratory assembly 100 and perhaps separately control each digit assembly 300 thereof. It is therefore contemplated that each digital assembly 300 may be directly controlled through a participant interface on dock housing 202 or by control signals communicated to an associated control module. In an exemplary embodiment, application programs for smartphones and other wireless handheld devices can function as a remote control sending control signals to a control module having a wireless receiver to control the operation of vibratory assembly 100 and at least one digit assembly 300 thereof.

In order to accommodate unlimited exploration of sexual stimulation and enjoyment in accordance with the devices described herein, participants and/or their partners might need to cue various positions for placement of articulating members and digit assemblies 300 worn thereon. To cue the various positions and generate unlimited levels of sexual intensity, a participant may need to employ one or more of the digit assemblies 300 described herein. Therefore, one or more kits may be provided containing one more different vibration pods for producing a wide range of sexual experiences. A kit of this type may include a plurality of vibratory assemblies with each vibratory assembly being configured to generate a desired level of stimulation. Each kit may include a single vibration pod having a plurality of different pads interchangeable therewith. The kit may alternatively have multiple pods in combination with one or more pads to enable interchangeability with a large range of sexual participants. Pods having LEDS of different colors and light patterns may be interchangeable with different motive sources and/or different pads to accommodate participant preferences without sacrificing the desired sexual effect.

One or more kits may include, along with one or more pods and one or more pads, accompanying interactive software applications that may be downloaded on a desktop or uploaded from a remote site onto a mobile device. Instructions for use of the software applications may also be included in the kit along with resources for accessing any social networking platforms that provide the participant with an interface for collaboration with other participants and potential participants over a social network. The kit may also include a mobile device having the software applications (pre-loaded for ready use by the participant. A system may be provided that includes one or more vibratory assemblies 100 as described herein. Such a system may combine vibratory assemblies 100 with a plurality of interchangeable vibrator components and a power source. In an exemplary embodiment, at least one of the plurality of interchangeable vibrator components and the vibratory assemblies may be in communication with at least one remote control communicating signals thereto. In another exemplary embodiment, at least one of the plurality of interchangeable vibrator components and the vibratory assemblies is a network-connected device in communication with one or more computing devices running at least one software application thereon (e.g., at least one sexual experience application). The system may further include a server in communication with the network-connected device and configured to perform actions including accessing the system over a network via a network interface. A participant may selectively perform methods suggested by such software applications and provide feedback representative of a participant's sexual experience using the system or any feature thereof.

Examples of different particular embodiments of each of the various components as well as different embodiments of the overall apparatus have been illustrated and described above. The examples illustrate particular combinations of control module and vibratory device design features, however other combinations and arrangements of the various inventive features can be implemented, and are intended to be encompassed within the spirit and scope of the present invention. Furthermore, variations and modifications other than those illustrated and described will be apparent to persons of ordinary skill in the art. It is intended that all such embodiments, examples, variations, combinations, and modifications thereon are meant to be encompassed within the spirit and scope of the present invention as set forth in the following claims.

Every document cited herein, including any cross-referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the invention has been described in certain embodiments, it will be understood that changes, additions, and modifications may be made to the respective articles forming the invention. Accordingly, no limitation should be imposed on the scope of this invention, except as set forth in the accompanying claims.

What is claimed is:

1. An expandable vibratory system for use by one or more participants, comprising:

a power source;

at least one first vibratory mechanism comprising:

at least one motive source in electrical communication with the power source;

at least one vibration pod in which the motive source is housed; and at least one pad having a lumen for insertion of the at least one vibration pod therewithin;

wherein the power source is located externally of the motive source and is positionable independently of the at least one first vibratory mechanism; and wherein the at least one first vibratory mechanism is configured to removably connect electrically with at least one second vibratory mechanism to create an expandable chain of vibratory mechanisms in operative communication with one another.

2. The expandable vibratory system of claim 1, wherein the power source is provided in a housing and is connected in parallel via a cable with the at least one first vibratory mechanism, and wherein:

the power source is selected from a standard battery, a rechargeable battery and a specialized battery operational with the at least one first vibratory mechanism; and one of the power source and the housing selectively includes at least one of a power switch and a participant interface thereon.

3. The expandable vibratory system of claim 1, wherein the at least one vibration pod includes a pod housing in which the at least one motive source is disposed in electrical communication with the power source, and the pod housing has a predetermined length, a predetermined width and a predetermined height that provides the pod housing with a generally low profile and a size adapted to be worn on at least one of the articulating members.

4. The expandable vibratory system of claim 3, wherein the at least one second vibratory mechanism comprises:

at least one second motive source in electrical communication with the power source;

at least one second vibration pod in which the second motive source is housed; and at least one second pad having a second lumen for insertion of the at least one second vibration pod therewithin;

wherein the power source is located externally of the second motive source and is positionable independently of the at least one second vibratory mechanism.

5. The expandable vibratory system of claim 4, wherein any of the first or second vibrator pods are adapted for use with fingers having a width in a range from about 10 mm to about 20 mm.

6. The expandable vibratory system of claim 4, wherein any of the first or second vibration pods are configured with respect to respective distances from a fingertip to a first knuckle on a finger and from the first knuckle to a second knuckle on the finger.

7. The expandable vibratory system of claim 3, wherein the pod housing contains at least two wires forming a circuit between the at least one motive source and an external device to control and power the motive source using a cable that contains the wires.

8. The expandable vibratory system of claim 1, wherein the at least one motive source includes one or more motors and each motor is selected from a motor fitted with an eccentric rotating weight, a solenoid actuator, a piezoelectric actuator, a cylindrical motor, a pan motor and combinations and equivalents thereof.

9. The expandable vibratory system of claim 1, wherein the at least one pad includes a body having one or more attachment loops integral therewith, and the pad body includes an external surface with elongate opposed side surfaces, opposed longitudinal surfaces, opposed extents and an internal surface delineating a lumen thereby.

10. The expandable vibratory system of claim 9, wherein each loop includes an arc connecting hinged extents of the loop disposed along the pad body and defining an orifice through which a participant inserts at least one digit of an articulating member.

11. The expandable vibratory system of claim 10, wherein the hinged extents depend generally from opposed side surfaces of the pad body such that each loop is offset from a longitudinal axis of the pad body, and the arc is pivotable along the pad body so that the arc may be rotated between an upright position relative to a longitudinal surface of the pad body and an inverted position relative to an opposed longitudinal surface of the pad body so that one or more digits of different sizes are insertable through the orifice.

12. The expandable vibratory system of claim 11, wherein at least one of the pad body and one or more loops incorporates at least one of a tactile element selected from a group of tactile elements including protrusions and recesses, and an aesthetic element selected from a group of aesthetic elements including one or more colors, materials, patterns and embellishments.

13. The expandable vibratory system of claim 1, wherein one or more controllers are in wireless communication with the expandable vibratory system over a network.

14. An expandable vibratory massager system for applying stimulation to human erogenous zones, comprising:

a plurality of removably electrically connectable vibration pods each comprising:

a housing having a plurality of exterior surfaces and a non-linear periphery; and at least one motive source retained by the housing; and an external device adapted to power and control the at least one motive source of each vibration pod when each vibration pod is electrically connected with the external device either directly or through another vibration pod, the external device spaced apart from and positionable independently of the vibration pods.

15. The expandable vibratory massager system of claim 14, further comprising one or more cables, wherein the plurality of removably electrically connectable vibration pods each further comprise any of a female or male connection adapted to removably electrically connect the vibration pods together via the one or more cables to create an expandable chain of the vibrations pods in operative communication with one another for enjoyment by one or plural participants.

16. The expandable vibratory massager system of claim 15, wherein at least one of the vibration pods is housed in at least one silicone pad having a body with one or more attachment loops integral therewith, and the pad body includes an external surface and an internal surface delineating a lumen thereby.

17. The expandable vibratory massager system of claim 16, wherein each loop includes an arc connecting hinged extents of the loop disposed along the pad body and defining an orifice through which a participant inserts at least one digit of an articulating member, and the hinged extents depend generally from opposed side surfaces of the pad body such that each loop is offset from a longitudinal axis of the pad body.

18. The expandable vibratory massager system of claim 17, wherein the arc is pivotable along the pad body so that the arc may rotated between an upright position relative to a longitudinal surface of the pad body and an inverted position relative to an opposed longitudinal surface of the pad body so that fingers of different sizes are insertable through the orifice.

19. A kit for providing erogenous stimulation to at least one participant, comprising:

a power source;

one or more vibratory assemblies for articulating members of at least one participant, each vibratory assembly comprising:

a vibratory mechanism comprising at least one motive source in electrical communication with the power source, the vibratory mechanism comprising:

one or more vibration pods each housing at least one motive source thereby; and one or more pads each having a lumen for insertion of one or more vibration pods therewithin;

wherein the power source is located externally of and is positionable independently of the motive source; and wherein the one or more vibratory assemblies are configured to removably connect electrically with each other to create an expandable chain of vibratory mechanisms in operative communication with one another.

20. The kit of claim 19, further comprising a network-connected device in communication with the power source and in communication with one or more computing devices running at least one software application thereon.

* * * * *